US008975433B2

(12) United States Patent
Nagahama et al.

(10) Patent No.: US 8,975,433 B2
(45) Date of Patent: Mar. 10, 2015

(54) 2-CYANOACRYLATE-PURIFYING METHOD

(75) Inventors: Yoshio Nagahama, Osaka (JP); Yukinori Nishino, Osaka (JP); Hiroaki Yamamoto, Osaka (JP)

(73) Assignee: Taoka Chemical Co., Ltd., Osaka (JP)

( * ) Notice: Subject to any disclaimer, the term of this patent is extended or adjusted under 35 U.S.C. 154(b) by 0 days.

(21) Appl. No.: 14/001,372

(22) PCT Filed: Feb. 24, 2012

(86) PCT No.: PCT/JP2012/054642

§ 371 (c)(1), (2), (4) Date: Aug. 23, 2013

(87) PCT Pub. No.: WO2012/117977

PCT Pub. Date: Sep. 7, 2012

(65) Prior Publication Data

US 2013/0331598 A1 Dec. 12, 2013

(30) Foreign Application Priority Data

Mar. 3, 2011 (JP) ................................ 2011-046605
Feb. 1, 2012 (JP) ................................ 2012-019375

(51) Int. Cl.
*C07C 253/34* (2006.01)
*C09J 4/00* (2006.01)

(52) U.S. Cl.
CPC . *C07C 253/34* (2013.01); *C09J 4/00* (2013.01)
USPC .......................................................... 558/443

(58) Field of Classification Search
CPC .................................................... C07C 253/34
USPC .......................................................... 558/443
See application file for complete search history.

(56) References Cited

U.S. PATENT DOCUMENTS

| | | | | |
|---|---|---|---|---|
| 7,709,676 | B2 | 5/2010 | Kanou et al. | |
| 8,168,736 | B2 | 5/2012 | Schmitt et al. | |
| 2007/0027335 | A1 | 2/2007 | Kanou et al. | |
| 2010/0174028 | A1 | 7/2010 | Schmitt et al. | |
| 2010/0210784 | A1 | 8/2010 | Schmitt et al. | |
| 2010/0286331 | A1 | 11/2010 | Schmitt et al. | |
| 2012/0255461 | A1* | 10/2012 | Nishino et al. | 106/287.25 |
| 2013/0225640 | A1* | 8/2013 | Kim | 514/345 |

FOREIGN PATENT DOCUMENTS

| | | | |
|---|---|---|---|
| JP | 04-124168 | A | 4/1992 |
| JP | 2007-126632 | A | 5/2007 |
| JP | 2010-235821 | A | 10/2010 |
| JP | 2010-532810 | A | 10/2010 |
| WO | WO 2004/106284 | A1 | 12/2004 |

OTHER PUBLICATIONS

International Search Report for corresponding International Application No. PCT/JP2012/054642 mailed Mar. 27, 2012.
Form PCT/ISA/237 for corresponding International Application No. PCT/JP2012/054642 dated Mar. 27, 2012.

* cited by examiner

*Primary Examiner* — Joseph Kosack
*Assistant Examiner* — Amanda L Aguirre
(74) *Attorney, Agent, or Firm* — Renner, Otto, Boisselle & Sklar, LLP

(57) ABSTRACT

Provided is a 2-cyanoacrylate-purifying method for decoloring a 2-cyanoacrylate which has been colored, and preventing further coloring of the 2-cyanoacrylate thus decolored. The 2-cyanoacrylate-purifying method includes the steps of: (a) adding a specific polyhydric aromatic compound to the 2-cyanoacrylate which has been colored; and (b) storing, at a temperature in a range of 0° C. to 40° C. for 0.5 day or more, the resulting mixture obtained in the step (a), and then subjecting the mixture to reduced pressure distillation.

4 Claims, No Drawings

2-CYANOACRYLATE-PURIFYING METHOD

TECHNICAL FIELD

The present invention relates to a 2-cyanoacrylate-purifying method.

BACKGROUND ART

A 2-cyanoacrylate adhesive agent has anionic polymerizability specific to 2-cyanoacrylate which is a main ingredient of 2-cyanoacrylate adhesive agent. The anionic polymerizability allows the 2-cyanoacrylate adhesive agent to start polymerization by, for example, a weak anion such as a slight amount of moisture adhered to a surface of an adherend, so that various materials can be tightly adhered to each other in a short time. For this reason, the 2-cyanoacrylate adhesive agent has been widely used as so-called instant glue in, for example, industrial, medical, and household fields.

Further, the 2-cyanoacrylate adhesive agent, which is generally transparent, has been used to adhere transparent plates or sheets, or used as an adhesive agent for optical components. Alternatively, the 2-cyanoacrylate adhesive agent is also suitably used in a field where adhesion is carried out with use of an adhesive agent in which a dye or a pigment is dissolved so as to utilize a color of the dye or the pigment. In such a field where an adhesive agent is required to be transparent, it has been reported that an adhesive whose main ingredient has a Hazen color number of 50 or more cannot be suitably used as an adhesive agent (see Patent Literature 1).

Meanwhile, 2-cyanoacrylate, which is a colorless and transparent liquid, has problems of (i) being colored to a color in a range of yellow to red due to raw materials or minute amounts of impurities produced during a production process, and (ii) being colored over time due to influence of heat, light, and humidity. In a case where 2-cyanoacrylate is colored to a degree being not less than a given level, not only in the field where an adhesive agent is required to be transparent but also in a general use, a commercial value of the 2-cyanoacrylate is significantly lost because such 2-cyanoacrylate may have to face a complaint about coloring of a liquid which is supposed to be colorless.

Given that presence of impurities is considered to be involved in coloring or acceleration of coloring of 2-cyanoacrylate, there have been presented (i) a method for producing 2-cyanoacrylate containing less acidic gas considered to be involved in production of impurities (see Patent Literature 2), and (ii) a method for preventing coloring of 2-cyanoacrylate under a generally-considered storage condition in which the 2-cyanoacrylate is stored with light shielded and at a low temperature and a low humidity. However, neither a literature nor a method has been known that presents a specific 2-cyanoacrylate-purifying method for reducing coloring of 2-cyanoacrylate which has been colored.

CITATION LIST

Patent Literatures

Patent Literature 1

Japanese Patent Application Publication, Tokukai, No. 2010-235821 A (Publication Date: Oct. 21, 2010)

Patent Literature 2

Japanese Patent Application Publication, Tokukaihei, No. 4-124168 A (Publication Date: Apr. 24, 1992)

SUMMARY OF INVENTION

Technical Problem

However, these methods, which are merely methods for preventing coloring of 2-cyanoacrylate, neither describe nor suggest decoloring effects. In addition, coloring preventing effects yielded by the methods are also limited and unsatisfactory. Therefore, a 2-cyanoacrylate-purifying method has been desired for decoloring 2-cyanoacrylate which has been colored, and preventing further coloring of the 2-cyanoacrylate thus decolored (improving hue stability of the 2-cyanoacrylate). An object of the present invention is to provide a 2-cyanoacrylate-purifying method for decoloring 2-cyanoacrylate which has been colored, and preventing further coloring of the 2-cyanoacrylate thus decolored.

Solution to Problem

The inventors of the present invention have accomplished the present invention as a result of their diligent study by finding that: a specific polyhydric aromatic compound exerts some action on a coloring substance and a causative substance each contained in a 2-cyanoacrylate, the causative substance being causative of coloring and changing into the coloring substance, so that the coloring substance and the causative substance are made harmless; these substances thus made harmless are then removed by reduced pressure distillation, so that a less colored 2-cyanoacrylate having a Hazen color number of 40 or less is obtained from a 2-cyanoacrylate having a Hazen color number of 50 or more; and further coloring of the less colored 2-cyanoacrylate thus obtained is considerably reduced. The inventors have thus accomplished the present invention. In other words, a 2-cyanoacrylate-purifying method in accordance with the present invention includes the steps of: (a) adding a specific polyhydric aromatic compound to a 2-cyanoacrylate having a Hazen color number of 50 or more; (b) storing, at a temperature in a range of 0° C. to 40° C. for 0.5 day or more, the resulting mixture obtained in the step (a); and (c) subjecting the mixture to reduced pressure distillation, so as to obtain the 2-cyanoacrylate which has improved in coloring to have a reduced Hazen color number of 40 or less, and prevent further coloring of the 2-cyanoacrylate thus obtained.

Advantageous Effects of Invention

According to the present invention, it is possible to provide a 2-cyanoacrylate such that: a specific polyhydric aromatic compound is added to a 2-cyanoacrylate having a Hazen color number of 50 or more, the 2-cyanoacrylate having been reported to be not suitably usable in the field where an adhesive agent is required to be transparent; the resulting mixture thus obtained is stored at a temperature in a range of 0° C. to 40° C. for 0.5 day or more, and then the mixture is subjected to reduced pressure distillation, so that the 2-cyanoacrylate which has improved in coloring immediately after being subjected to the reduced pressure distillation is obtained, and further coloring of the 2-cyanoacrylate thus obtained is prevented.

DESCRIPTION OF EMBODIMENTS

A 2-cyanoacrylate represented by formula (2) is suitably used as a 2-cyanoacrylate of the present invention.

[Chem. 1]

(2)

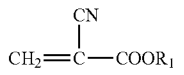

wherein $R_1$ represents a aliphatic hydrocarbon group, an alicyclic hydrocarbon group, or an aromatic hydrocarbon group which is saturated or unsaturated and may be substituted with a C1 to C16 substituent.

Specific examples of the 2-cyanoacrylate of the present invention include 2-cyanoacrylate esters such as methyl 2-cyanoacrylate, ethyl 2-cyanoacrylate, n-propyl 2-cyanoacrylate, isopropyl 2-cyanoacrylate, n-butyl 2-cyanoacrylate, isobutyl 2-cyanoacrylate, sec-butyl 2-cyanoacrylate, octyl 2-cyanoacrylate, neopentyl 2-cyanoacrylate, cyclohexyl 2-cyanoacrylate, ethylhexyl 2-cyanoacrylate, dodecyl 2-cyanoacrylate, allyl 2-cyanoacrylate, methoxyethyl 2-cyanoacrylate, ethoxyethyl 2-cyanoacrylate, methoxypropyl 2-cyanoacrylate, benzil 2-cyanoacrylate, phenyl 2-cyanoacrylate, chloroethyl 2-cyanoacrylate, and tetrahydrofurfuryl 2-cyanoacrylate. Further, these 2-cyanoacrylates can be used alone or in combination of two or more kinds.

A crude 2-cyanoacrylate to which the present invention is applied is a 2-cyanoacrylate having a Hazen color number of 50 or more. A method for producing a 2-cyanoacrylate is typified by a method in which a 2-cyanoacrylate is obtained by condensing, in an organic solvent, cyanoacetate and formaldehyde in the presence of a basic catalyst, and then depolymerizing an obtained condensate at a high temperature and a reduced pressure in an acidic gas flow in the presence of a polymerization inhibitor and a depolymerizing catalyst. By cohobating this 2-cyanoacrylate, it is possible to obtain a colorless and transparent 2-cyanoacrylate which generally has a Hazen color number in a range of 20 to 30. Note, however, that a 2-cyanoacrylate, which is a very unstable substance, is likely to have a higher Hazen color number in a case where minute amounts of impurities are contained in a raw material or acidic gas is excessively used during a production process. Further, the 2-cyanoacrylate is also likely to have a higher Hazen color number in a case where the 2-cyanoacrylate is exposed, for a long time, to a temperature being not less than a given temperature, or exposed to a high temperature even for a short time. Such a crude 2-cyanoacrylate that is normally cohobated does not have a Hazen color number of less than 50. Alternatively, even the crude 2-cyanoacrylate, which initially has a Hazen color number of less than 50, may be colored, due to a change over time, to have a Hazen color number greatly exceeding 50.

The present invention has been accomplished by a method including the steps of: (a) adding, to such a colored crude 2-cyanoacrylate, at least one kind of an polyhydric aromatic compound selected from the group consisting of resorcin and a compound represented by formula (1):

[Chem. 2]

(1)

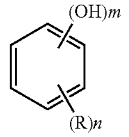

wherein R independently represents a hydrogen atom, a carboxy group, an alkoxycarbonyl group, or an alkoxyalkyloxycarbonyl group; and m is an integer of 3 to 5, n is an integer of 1 to 3, and m+n=6; (b) storing, at a temperature in a range of 0° C. to 40° C. for 0.5 day or more, the resulting mixture obtained in the step (a); and (c) subjecting the mixture to reduced pressure distillation so as to remove each of a low-boiling-point fraction and a high-boiling-point fraction of certain ranges.

Examples of an polyhydric aromatic compound of the present invention include trihydroxybenzenes such as pyrogallol, 1,2,4-trihydroxybenzene, gallic acid alkyl esters containing a C1 to C4 alkyl group such as gallic acid methyl ester, gallic acid ethyl ester, gallic acid propyl ester, and gallic acid butyl ester, gallic acid alkoxyalkyl esters containing a C1 to C4 alkoxyalkyl group such as gallic acid methoxy methyl ester, gallic acid methoxy ethyl ester, gallic acid methoxy propyl ester, gallic acid ethoxy methyl ester, and gallic acid ethoxy ethyl ester, phloroglucinol, benzene tetraol, benzene hexaol, resorcin, and gallic acid. Of these polyhydric aromatic compounds, gallic acid, gallic acid alkyl esters containing a C1 to C4 alkyl group, gallic acid alkoxyalkyl esters containing a C1 to C4 alkoxyalkyl group, trihydroxy benzenes, and resorcin are preferable. The polyhydric aromatic compounds of the present invention can be used alone or in combination of two or more kinds as needed. The polyhydric aromatic compound(s) is/are used in an amount normally of 0.05 wt % to 5 wt %, preferably of 0.1 wt % to 3 wt %, and more preferably of 0.1 wt % to 1 wt %, with respect to the crude 2-cyanoacrylate. The polyhydric aromatic compound(s) which is/are used in an amount of less than 0.05 wt % brings about a less powerful coloring reducing effect. Meanwhile, the polyhydric aromatic compound(s) which is/are used in an amount of more than 5 wt % may cause a deterioration in quality of 2-cyanoacrylate.

After at least one kind of an polyhydric aromatic compound selected from the group consisting of resorcin and aromatic polyhydric hydroxy compounds represented by formula (1) is added to a crude 2-cyanoacrylate before reduced pressure distillation, the reduced pressure distillation is not carried out until completion of storage of the resulting mixture at a temperature in a range of 0° C. to 40° C., preferably of 10° C. to 30° C. for a period of 0.5 day or more. During this period, the mixture is stored in a sealed container while being stirred or unstirred. If the temperature is far below 0° C. during the period, the decoloring effect and the like thus obtained may be insufficient. If the temperature is higher than 40° C. during the period, 2-cyanoacrylate may have a poor quality due to a side reaction. Further, the period is 0.5 day (12 hours) to 30 days, and preferably 1 day to 14 days. The period which is less than 0.5 day cannot sufficiently bring about a decoloring effect and the like, and the period which is more than 30 days is economically unpreferable because of a decrease in production efficiency.

It is not particularly limited under what condition the distillation is carried out after the period has passed. However, the distillation is normally carried out under a reduced pressure of 0.1 kPa to 2 kPa. For example, in a case where the distillation is carried out under a reduced pressure of 0.6 kPa, a low-boiling-point fraction starts to be distilled at a distillation temperature of around 30° C. A main fraction obtained at a distillation temperature in a range of 60° C. to 80° C. corresponds to an ingredient of a purified 2-cyanoacrylate of the present invention. A low-boiling-point fraction herein refers to a fraction which is obtained during a period between a point in time at which an first fraction starts to be distilled after the start of the distillation and a point in time at which the first fraction changes to a main fraction after a weight ratio of the first fraction to the crude 2-cyanoacrylate reaches a given weight ratio. Specifically, even though a fraction identical to that obtained at a boiling point of a 2-cyanoacrylate is obtained in the present invention, the fraction is regarded as a low-boiling-point fraction until a weight ratio of the fraction to the 2-cyanoacrylate reaches a weight ratio described herein. Similarly, as to a high-boiling-point fraction, even though a fraction identical to that obtained at a boiling point of a 2-cyanoacrylate is obtained in the present invention, the fraction is regarded as a high-boiling-point fraction when a weight ratio of a later fraction including a still residue to the 2-cyanoacrylate reaches a weight ratio described herein. Note that a removal ratio described herein of each of the low-boiling-point fraction and the high-boiling-point fraction refers to a value of wt % of each of the low-boiling-point fraction and the high-boiling-point fraction with respect to the crude 2-cyanoacrylate to which an polyhydric aromatic compound, various stabilizers, and the like have not been added. The removal ratio of the low-boiling-point fraction varies depending on a coloring degree of the crude 2-cyanoacrylate. However, the removal ratio is normally in a range of 5 wt % to 40 wt %, and preferably 10 wt % to 30 wt % with respect to the crude 2-cyanoacrylate. The removal ratio which is less than 5 wt % brings about a less powerful coloring reducing effect, and the removal ratio which is not less than 40 wt % is economically unadvantageous. Further, the removal ratio of the high-boiling-point fraction including a still residue is in a range of 10 wt % to 30 wt %, and preferably of 10 wt % to 20 wt % with respect to the crude 2-cyanoacrylate. The removal ratio which is less than 10 wt % brings about a less powerful coloring reducing effect, and the removal ratio which is not less than 30 wt % is economically unadvantageous.

Further, hydroquinone and phosphorus pentaoxide which are conventionally used during distillation of a 2-cyanoacrylate can be used as needed. Moreover, a stabilizer (e.g., an anion polymerization inhibitor such as sulfur dioxide, methanesulfonic acid, p-toluenesulfonic acid, boron trifluoride diethyl ether, fluoroboric acid, or trialkyl borate, or a radical polymerization inhibitor such as hydroquinone or hydroquinone monomethyl ether), a plasticizer (e.g., dimethyl phthalate, diethyl phthalate, dibutyl phthalate, 2-ethylhexyl phthalate, or di-isodecyl phthalate), a coloring agent, a perfume, a solvent, a hardening accelerator, a strength improving agent, and aliphatic polyhydric carboxylic acid, which are conventionally used as additives, can be appropriately used to be mixed, according to purpose, as additives to a purified 2-cyanoacrylate obtained by the distillation, provided that the additives do not inhibit stability of a 2-cyanoacrylate monomer.

That is, the present invention provides the following [1] through [3].

[1] A 2-cyanoacrylate-purifying method for purifying a crude 2-cyanoacrylate having a Hazen color number of 50 or more, said 2-cyanoacrylate-purifying method comprising the steps of: (a) adding to, the crude 2-cyanoacrylate, at least one kind of an polyhydric aromatic compound selected from the group consisting of resorcin and a compound represented by formula (1); (b) storing, at a temperature in a range of 0° C. to 40° C. for 0.5 day or more, the resulting mixture obtained in the step (a); (c) subjecting the mixture to reduced pressure distillation so as to remove (i) a low-boiling-point fraction by 5 wt % to 40 wt % with respect to the crude 2-cyanoacrylate, and (ii) a high-boiling-point fraction by 10 wt % to 30 wt % with respect to the crude 2-cyanoacrylate, so as to obtain a purified 2-cyanoacrylate having a Hazen color number of 40 or less.

[Chem. 3]

(1)

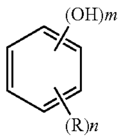

wherein R independently represents a hydrogen atom, a carboxy group, an alkoxycarbonyl group, or an alkoxyalkyloxycarbonyl group; and m is an integer of 3 to 5, n is an integer of 1 to 3, and m+n=6.

[2] The 2-cyanoacrylate-purifying method described in [1], wherein the polyhydric aromatic compound is at least one kind selected from the group consisting of gallic acid, gallic acid alkyl esters containing a C1 to C4 alkyl group, gallic acid alkoxyalkyl esters containing a C1 to C4 alkoxyalkyl group, trihydroxy benzenes, and resorcin.

[3] The 2-cyanoacrylate-purifying method described in [2] or [3], wherein the low-boiling-point fraction is removed by 10 wt % to 30 wt % with respect to the crude 2-cyanoacrylate during the reduced pressure distillation.

(Measurement of Coloring Degree (Hue) and Hue Stability)

A Hazen color number indicative of a coloring degree (hue) of a 2-cyanoacrylate of the present invention was measured by a method based on JIS K0071-1.

As to hue stability of an adhesive composition, a hue of each adhesive composition which hue was obtained after the each adhesive composition had been stored at a temperature of 70° C. for 1 week was measured in a method similar to the method by which the Hazen color number was measured. A result of this measurement, which result cannot be unconditionally determined depending on a storage container and a storage condition, is substantially equivalent to a change in hue of an adhesive composition stored at a room temperature for approximately 1 year.

(Purity)

In Examples below, a purity of a 2-cyanoacrylate was measured by a gas chromatography analysis carried out under the following condition. Note that a purity described in each of Examples and Comparative Examples of the present invention is an area percentage of a 2-cyanoacrylate obtained under the following analysis condition.

Condition of Analysis by Gas Chromatography
Apparatus Used: Shimazu 14A
Column: Silicon XE-60
Column Temperature: 190° C.
Detector: FID
Carrier: $N_2$ (40 ml/min)

EXAMPLES

The following will more specifically describe the present invention with reference to Examples.

Preparation 1 of Crude 2-cyanoacrylate reproduces a case where a trouble such as a device trouble or an operation trouble occurred during depolymerization, the crude 2-cyanoacrylate might be exposed to a high temperature for a long time than necessary, so that the crude 2-cyanoacrylate is colored undesirably. In Preparation 1, the crude 2-cyanoacrylate having a Hazen color number of 50 or more was obtained. In Preparations 2 and 3 of Crude 2-cyanoacrylate, an ethyl-2-cyanoacrylate which is commercially available as a reagent and has a normal purity of 99% was exposed to sunlight by the window so that coloring of the ethyl-2-cyanoacrylate was forcibly progressed. As a result, a crude 2-cyanoacrylate having a Hazen color number of 50 or more was obtained. Then, a part of the crude 2-cyanoacrylate was further exposed to a high temperature, so that the crude 2-cyanoacrylate having a higher coloring degree was obtained.

Preparation Example 1

Preparation 1 of Crude 2-cyanoacrylate

In a three neck flask provided with a stirrer, thermometer, a water separator, and a dropping funnel, 360 g of paraformaldehyde, 1200 g of toluene, and 1.2 g of piperidine were introduced. While the resulting mixture was maintained at a temperature of 80° C. to 90° C., 1356 g of ethyl cyanoacetate was dropped over 60 minutes under stirring. After the dropping was completed, while azeothropic separation of generated water was being carried out, the mixture was reacted under reflux for approximately 6 hours until a theoretical amount of water was distilled. As a result, a toluene solution of a polymer was obtained. After this solution was desolvated at a normal pressure, 40 g of phosphorus pentaoxide and 12 g of hydroquinone were added to the solution and sufficiently mixed with the solution. After the resulting mixture was desolvated under a reduced pressure, the mixture was heated to a temperature in a range of 150° C. to 200° C. under a reduced pressure of 0.6 kPa so that depolymerization was carried out. In order to expose the mixture to more heat, depolymerization, which is normally completed in 2 hours, was carried out over 5 hours. As a result, 1400 g of a crude 2-cyanoacrylate was obtained. Then, a Hazen color number of the crude 2-cyanoacrylate was measured to be 150.

Preparation Example 2

Preparation 2 of Crude 2-Cyanoacrylate

After 2500 g of an ethyl-2-cyanoacrylate (having a purity of 99% and a Hazen color number of 30) that is a reagent was introduced in a transparent plastic container and then left to stand still by the window for 1 month, whereby the ethyl-2-cyanoacrylate having a Hazen color number of 80 was obtained. Then, 2,000 g of the ethyl-2-cyanoacrylate was introduced in a polyethylene container, and left to stand still at a temperature of 70° C. for 1 week. As a result, a Hazen color number of the ethyl-2-cyanoacrylate was measured to be 150.

Preparation Example 3

The following Comparative Examples and Examples each used, as it is, the remaining 500 g of the ethyl-2-cyanoacrylate which was obtained in Preparation Example 2 by being left to stand still by the window for 1 month to have a Hazen color number of 80.

Preparation Example 4

2,000 g of the ethyl-2-cyanoacrylate, which, in Preparation Example 2, had been left to stand still by the window for 1 month and then had a Hazen color number of 80, was introduced in the polyethylene container, and then left to stand still at a temperature of 70° C. for 1 week. Then, the resulting ethyl-2-cyanoacrylate had a Hazen color number of 150. 500 g of the ethyl-2-cyanoacrylate having a Hazen color number of 150 was left to stand still at a temperature of 70° C. for another week. Then, a Hazen color number of the ethyl-2-cyanoacrylate was measured to be 250.

While carrying out monitoring so that a given first fraction and a main fraction could be obtained, the following Comparative Examples and Examples each appropriately adjusted a distillation temperature and a distillation time in addition to a degree of reduced pressure which degree is described in each of these examples. Note that ratios of each of a low-boiling-point fraction and a high-boiling-point fraction are wt % with respect to an initially placed crude ethyl-2-cyanoacrylate.

Comparative Example 1

To 100 g of the crude ethyl-2-cyanoacrylate obtained in Preparation Example 1, 0.5 g of hydroquinone and 0.1 g of phosphorus pentaoxide were added as polymerization inhibitors. The resulting mixture was distilled under a reduced pressure of 1 kPa so that 3 g of a low-boiling-point fraction (3% low-boiling-point fraction) was distilled off. Then, 82 g of a purified ethyl-2-cyanoacrylate (having a purity of 99%) was obtained as a main fraction of the distillation. Meanwhile, a high-boiling-point fraction (15% high-boiling-point fraction) including a later fraction and a still residue measured 15.5 g. Then, an adhesive composition was prepared by adding 0.0008 g of fluoroboric acid and 0.08 g of hydroquinone to 80 g of the purified ethyl-2-cyanoacrylate. A Hazen color number of the adhesive composition was measured to be 60. The adhesive composition was introduced in a polyethylene container and left to stand still at a temperature of 70° C. for 1 week. Then, a Hazen color number of the adhesive composition was measured to be 120.

Comparative Example 2

To 100 g of the crude ethyl-2-cyanoacrylate obtained in Preparation Example 1, 0.5 g of hydroquinone and 0.1 g of phosphorus pentaoxide were added as polymerization inhibitors. The resultaning mixture was distilled under a reduced pressure of 1 kPa so that 30 g of a low-boiling-point fraction (30% low-boiling-point fraction) was distilled off. Then, 40 g of a purified ethyl-2-cyanoacrylate (having a purity of 99%) was obtained as a main fraction of the distillation. Meanwhile, a high-boiling-point fraction (30% high-boiling-point fraction) including a later fraction and a still residue measured 30 g. Then, an adhesive composition was prepared by adding 0.0004 g of fluoroboric acid and 0.04 g of hydroquinone to 40 g of the purified ethyl-2-cyanoacrylate. A Hazen color number of the adhesive composition was measured to be 60. The adhesive composition was introduced in a polyethylene container and left to stand still at a temperature of 70° C. for 1 week. Then a Hazen color number of the adhesive composition was measured to be 100.

Comparative Example 3

To 100 g of the crude 2-cyanoacrylate obtained in Preparation Example 2, 0.1 g of resorcin was added and mixed, and then the resulting mixture was left to stand still at a temperature of 40° C. for 2 days. Thereafter, an adhesive composition was prepared by adding 0.0004 g of fluoroboric acid and 0.04 g of hydroquinone to 40 g of the ethyl-2-cyanoacrylate. A Hazen color number of the adhesive composition, which had not been subjected to reduced pressure distillation, was measured to be 70. The adhesive composition was introduced in a polyethylene container and left to stand still at a temperature of 70° C. for 1 week. Then a Hazen color number of the adhesive composition was measured to be 120.

Comparative Example 4

To 100 g of the crude ethyl-2-cyanoacrylate obtained in Preparation Example 2, 0.1 g of 2,6-di-tert-butylphenol was added and mixed, and then left to stand still at a temperature of 40° C. for 2 days. Then, 0.5 g of hydroquinone and 0.1 g of phosphorus pentaoxide were added as polymerization inhibitors to 100 g of the crude ethyl-2-cyanoacrylate. The resulting mixture was distilled under a reduced pressure of 0.3 kPa so that 3 g of first fraction (3% low-boiling-point fraction) was distilled off. Then, 82 g of a purified ethyl-2-cyanoacrylate (having a purity of 99%) was obtained as a main fraction of the distillation. Meanwhile, a high-boiling-point fraction (15% high-boiling-point fraction) including a later fraction and a still residue measured 15.3 g. Then, an adhesive composition was prepared by adding 0.00075 g of fluoroboric acid and 0.075 g of hydroquinone to 75 g of the purified ethyl-2-cyanoacrylate. A Hazen color number of the adhesive composition was measured to be 80. The adhesive composition was introduced in a polyethylene container and left to stand still at a temperature of 70° C. for 1 week. Then, a Hazen color number of the adhesive composition was measured to be 120.

Comparative Example 5

To 100 g of the crude ethyl-2-cyanoacrylate obtained in Preparation Example 2, 1 g of resorcin was added and mixed, and then left to stand still at a temperature of 20° C. for 5 days. Then, 0.5 g of hydroquinone and 0.1 g of phosphorus pentaoxide were added as polymerization inhibitors to 100 g of the crude ethyl-2-cyanoacrylate. A resultant mixture was distilled under a reduced pressure of 0.3 kPa so that 3.2 g of first fraction (3% low-boiling-point fraction) was distilled off. Then, 82.5 g of a purified ethyl-2-cyanoacrylate (having a purity of 99%) was obtained as a main fraction of the distillation. Meanwhile, a high-boiling-point fraction (15% high-boiling-point fraction) including a later fraction and a still residue measured 15.1 g. Then, an adhesive composition was prepared by adding 0.00082 g of fluoroboric acid and 0.082 g of hydroquinone to 82 g of the purified ethyl-2-cyanoacrylate. A Hazen color number of the adhesive composition was measured to be 70. The adhesive composition was introduced in a polyethylene container and left to stand still at a temperature of 70° C. for 1 week. A Hazen color number of the adhesive composition was measured to be 110.

Comparative Example 6

To 100 g of the crude ethyl-2-cyanoacrylate obtained in Preparation Example 2, 1 g of pyrogallol was added and mixed, and then left to stand still at a temperature of 40° C. for 5 days. Then, 0.5 g of hydroquinone and 0.1 g of phosphorus pentaoxide were added as polymerization inhibitors to 100 g of the crude ethyl-2-cyanoacrylate. The resulting mixture was distilled under a reduced pressure of 0.3 kPa so that 3.1 g of first fraction (3% low-boiling-point fraction) was distilled off. Then, 82.6 g of a purified ethyl-2-cyanoacrylate (having a purity of 99%) was obtained as a main fraction of the distillation. Meanwhile, a high-boiling-point fraction (15% high-boiling-point fraction) including a later fraction and a still residue measured 15.3 g. Then, an adhesive composition was prepared by adding 0.00082 g of fluoroboric acid and 0.082 g of hydroquinone to 82 g of the purified ethyl-2-cyanoacrylate. A Hazen color number of the adhesive composition was measured to be 60. The adhesive composition was introduced in a polyethylene container and left to stand still at a temperature of 70° C. for 1 week. Then, a Hazen color number of the adhesive composition was measured to be 110.

Comparative Example 7

To 100 g of the crude ethyl-2-cyanoacrylate obtained in Preparation Example 2, 0.5 g of gallic acid methoxy ethyl ester was added and mixed, and then was left to stand still at a temperature of 40° C. for 1 day. Then, 0.5 g of hydroquinone and 0.1 g of phosphorus pentaoxide were added as polymerization inhibitors to 100 g of the crude ethyl-2-cyanoacrylate. The resulting mixture was distilled under a reduced pressure of 0.3 kPa so that 4.2 g of first fraction (4% low-boiling-point fraction) was distilled off. Then, 76.2 g of a purified ethyl-2-cyanoacrylate (having a purity of 99%) was obtained as a main fraction of the distillation. Meanwhile, a high-boiling-point fraction (20% high-boiling-point fraction) including a later fraction and a still residue measured 19.9 g. Then, an adhesive composition was prepared by adding 0.00075 g of fluoroboric acid and 0.075 g of hydroquinone to 75 g of the purified ethyl-2-cyanoacrylate. A Hazen color number of the adhesive composition was measured to be 60. The adhesive composition was introduced in a polyethylene container and left to stand still at a temperature of 70° C. for week. Then, a Hazen color number of the adhesive composition was measured to be 90.

Comparative Example 8

To 100 g of the crude ethyl-2-cyanoacrylate obtained in Preparation Example 3, 0.5 g of hydroquinone and 0.1 g of phosphorus pentaoxide were added as polymerization inhibitors. The resulting mixture was distilled under a reduced pressure of 1 kPa so that 29.9 g of low-boiling-point fraction (30% low-boiling-point fraction) was distilled off. Then, 40.2 g of a purified ethyl-2-cyanoacrylate (having a purity of 99%) was obtained as a main fraction of the distillation. Meanwhile, a high-boiling-point fraction (30% high-boiling-point fraction) including a later fraction and a still residue measured 30.1 g. Then, an adhesive composition was prepared by adding 0.0004 g of fluoroboric acid and 0.04 g of hydroquinone to 40 g of the purified ethyl-2-cyanoacrylate. A Hazen color number of the adhesive composition was measured to be 60. The adhesive composition was introduced in a polyethylene container and left to stand still at a temperature of 70° C. for 1 week. Then, a Hazen color number of the adhesive composition was measured to be 100.

Comparative Example 9

To 100 g of the crude ethyl-2-cyanoacrylate obtained in Preparation Example 3, 1.0 g of gallic acid was added and mixed, and then left to stand still at a temperature of 20° C. for 5 days. Then, 0.5 g of hydroquinone and 0.1 g of phosphorus pentaoxide were added as polymerization inhibitors to 100 g of the crude ethyl-2-cyanoacrylate. The resulting mixture was distilled under a reduced pressure of 0.3 kPa so that 3.1 g of first fraction (3% low-boiling-point fraction) was distilled off. Then, 77.2 g of purified ethyl-2-cyanoacrylate (having a purity of 99%) was obtained as a main fraction of the distillation. Meanwhile, a high-boiling-point fraction (21% high-boiling-point fraction) including a later fraction and a still residue measured 20.7 g. Then, an adhesive composition was prepared by adding 0.00075 g of fluoroboric acid and 0.075 g of hydroquinone to 75 g of the purified ethyl-2-cyanoacrylate. A Hazen color number of the adhesive composition was measured to be 60. The adhesive composition was introduced in a polyethylene container and left to stand still at a temperature of 70° C. for 1 week. Then, a Hazen color number of the adhesive composition was measured to be 90.

Comparative Example 10

To 100 g of the crude ethyl-2-cyanoacrylate obtained in Preparation Example 3, 1.0 g of catechol was added and mixed, and then left to stand still at a temperature of 30° C. for 5 days. Then, 0.5 g of hydroquinone and 0.1 g of phosphorus pentaoxide were added as polymerization inhibitors to 100 g of the crude ethyl-2-cyanoacrylate. The resulting mixture was distilled under a reduced pressure of 0.3 kPa so that 29.9 g of first fraction (30% low-boiling-point fraction) was distilled off. Then, 50.5 g of purified ethyl-2-cyanoacrylate (having a purity of 99%) was obtained as a main fraction of the distillation. Meanwhile, a high-boiling-point fraction (21% high-boiling-point fraction) including a later fraction and a still residue measured 20.7 g. Then, an adhesive composition was prepared by adding 0.0005 g of fluoroboric acid and 0.05 g of hydroquinone to 50 g of the purified ethyl-2-cyanoacrylate. A Hazen color number of the adhesive composition was measured to be 60. The adhesive composition was introduced in a polyethylene container and left to stand still at a temperature of 70° C. for 1 week. Then, a Hazen color number of the adhesive composition was measured to be 100.

Example 1

To 100 g of the crude ethyl-2-cyanoacrylate obtained in Preparation Example 1, 0.1 g of gallic acid methoxy ethyl ester was added and mixed, and then was left to stand still at a temperature of 40° C. for 2 days. Then, 0.5 g of hydroquinone and 0.1 g of phosphorus pentaoxide were added as polymerization inhibitors to 100 g of the crude ethyl-2-cyanoacrylate. The resulting mixture was distilled under a reduced pressure of 0.3 kPa so that 10 g of first fraction (10% low-boiling-point fraction) was distilled off. Then, 70 g of purified ethyl-2-cyanoacrylate (having a purity of 99%) was obtained as a main fraction of the distillation. Meanwhile, a high-boiling-point fraction (20% high-boiling-point fraction) including a later fraction and a still residue measured 20.5 g. Then, an adhesive composition was prepared by adding 0.00070 g of fluoroboric acid and 0.070 g of hydroquinone to 70 g of the purified ethyl-2-cyanoacrylate. A Hazen color number of the adhesive composition was measured to be 30. The adhesive composition was introduced in a polyethylene container and left to stand still at a temperature of 70° C. for week. Then, a Hazen color number of the adhesive composition was measured to be 50.

Example 2

Except that (a) 2 wt % of a gallic acid methoxy ethyl ester, which is an polyhydric aromatic compound, was added and (b) a still standing (storage) period was set to 1 day, the same process as in Example 1 was carried out such that a crude ethyl-2-cyanoacrylate identical to that of Example 1 was used, and stored and distilled under the same condition as that of Example 1 so that an identical adhesive composition was prepared with respect to an obtained purified ethyl-2-cyanoacrylate. A Hazen color number of this adhesive composition was measured to be 30. The adhesive composition was introduced in a polyethylene container and left to stand still at a temperature of 70° C. for 1 week. Then, a Hazen color number of the adhesive composition was measured to be 50.

Example 3

Except that (a) 0.5 wt % of a gallic acid methoxy ethyl ester, which is an polyhydric aromatic compound, was added and (b) a still standing (storage) temperature was set to 20° C., and (c) a still standing (storage) period was set to 10 days, the same process as in Example 1 was carried out such that a crude ethyl-2-cyanoacrylate identical to that of Example 1 was used, and stored and distilled under the same condition as that of Example 1 so that an identical adhesive composition was prepared with respect to an obtained purified ethyl-2-cyanoacrylate. A Hazen color number of this adhesive composition was measured to be 20. The adhesive composition was introduced in a polyethylene container and left to stand still at a temperature of 70° C. for 1 week. Then, a Hazen color number of the adhesive composition was measured to be 40.

Example 4

To 100 g of the crude ethyl-2-cyanoacrylate obtained in Preparation Example 1, 0.1 g of gallic acid was added and mixed, and then was stored at a temperature of 20° C. for 10 days. Afterward, 0.5 g of hydroquinone and 0.1 g of phosphorus pentaoxide were added as polymerization inhibitors to 100 g of the crude ethyl-2-cyanoacrylate. The resulting mixture was distilled under a reduced pressure of 0.3 kPa so that 5 g of first fraction (5% low-boiling-point fraction) was distilled off. Then, 85 g of a purified ethyl-2-cyanoacrylate (having a purity of 99%) was obtained as a main fraction of the distillation. Meanwhile, a high-boiling-point fraction (10% high-boiling-point fraction) including a later fraction and a still residue measured 10.2 g. Then, an adhesive composition was prepared by adding 0.00075 g of fluoroboric acid and 0.075 g of hydroquinone to 75 g of the purified ethyl-2-cyanoacrylate. A Hazen color number of the adhesive composition was measured to be 30. The adhesive composition was introduced in a polyethylene container and left to stand still at a temperature of 70° C. for 1 week. Then, a Hazen color number of the adhesive composition was measured to be 50.

Example 5

Except that distillation that (a) a first fraction was set to 40 g (40% low-boiling-point fraction), (b) a main fraction was set to 30 g (30% high-boiling-point fraction), and (c) a high-boiling-point fraction was set to 30.5 g (30% high-boiling-point fraction), the same process as in Example 4 was carried out so that an identical adhesive composition was prepared with respect to an obtained purified ethyl-2-cyanoacrylate. A Hazen color number of this adhesive composition was measured to be 10. The adhesive composition was introduced in a polyethylene container and left to stand still at a temperature of 70° C. for 1 week. Then, a Hazen color number of the adhesive composition was measured to be 30.

Example 6

To 100 g of the crude ethyl-2-cyanoacrylate obtained in Preparation Example 2, 1 g of pyrogallol was added and mixed, and then was left to still stand at a temperature of 10° C. for 15 days. Then, 0.5 g of hydroquinone and 0.1 g of phosphorus pentaoxide were added as polymerization inhibitors to 100 g of the crude ethyl-2-cyanoacrylate. The resulting mixture was distilled under a reduced pressure of 0.3 kPa so that 20 g of first fraction (20% low-boiling-point fraction) was distilled off. Then, 60 g of purified ethyl-2-cyanoacrylate (having a purity of 99%) was obtained as a main fraction of the distillation. Meanwhile, a high-boiling-point fraction (20% high-boiling-point fraction) including a later fraction and a still residue measured 20.3 g. Then, an adhesive composition was prepared by adding 0.0006 g of fluoroboric acid and 0.06 g of hydroquinone to 60 g of the purified ethyl-2-cyanoacrylate. A Hazen color number of the adhesive composition was measured to be 30. The adhesive composition was introduced in a polyethylene container and stored at a temperature of 70° C. for 1 week. Then, a Hazen color number of the adhesive composition was measured to be 40.

Example 7

To 100 g of the crude ethyl-2-cyanoacrylate obtained in Preparation Example 2, 1 g of pyrogallol was added and mixed, and then was left to stand still at a temperature of 30° C. for 15 days. Then, 0.5 g of hydroquinone and 0.1 g of phosphorus pentaoxide were added as polymerization inhibitors to 100 g of the crude ethyl-2-cyanoacrylate. The resulting mixture was distilled under a reduced pressure of 0.3 kPa so that 20 g of first fraction (20% low-boiling-point fraction) was distilled off. Then, 65 g of purified ethyl-2-cyanoacrylate (having a purity of 99%) was obtained as a main fraction of the distillation. Meanwhile, a high-boiling-point fraction (15% high-boiling-point fraction) including a later fraction and a still residue measured 15.3 g. Then, an adhesive composition was prepared by adding 0.00065 g of fluoroboric acid and 0.065 g of hydroquinone to 65 g of the purified ethyl-2-cyanoacrylate. A Hazen color number of the adhesive composition was measured to be 30. The adhesive composition was introduced in a polyethylene container and left to stand still at a temperature of 70° C. for 1 week. A Hazen color number of the adhesive composition was measured to be 50.

Example 8

To 100 g of the crude ethyl-2-cyanoacrylate obtained in Preparation Example 2, 5 g of resorcin was added and mixed, and then was left to stand still at a temperature of 20° C. for 30 days. Then, 0.5 g of hydroquinone and 0.1 g of phosphorus pentaoxide were added as polymerization inhibitors to 100 g of the crude ethyl-2-cyanoacrylate. A resultant mixture was distilled under a reduced pressure of 0.3 kPa so that 15 g of first fraction (15% low-boiling-point fraction) was distilled off. Then, 65 g of purified ethyl-2-cyanoacrylate (having a purity of 99%) was obtained as a main fraction of the distillation. Meanwhile, a high-boiling-point fraction (20% high-boiling-point fraction) including a later fraction and a still residue measured 20.5 g. Then, an adhesive composition was prepared by adding 0.0002 g of fluoroboric acid and 0.02 g of hydroquinone to 20 g of the purified ethyl-2-cyanoacrylate. A Hazen color number of the adhesive composition was measured to be 30. The adhesive composition was introduced in a polyethylene container and left to stand still at a temperature of 70° C. for 1 week. A Hazen color number of the adhesive composition was measured to be 80.

Example 9

To 100 g of the crude ethyl-2-cyanoacrylate obtained in Preparation Example 1, 1 g of gallic acid was added and mixed, and then was left to stand still at a temperature of 20° C. for 1 days. Then, 0.5 g of hydroquinone and 0.1 g of phosphorus pentaoxide were added as polymerization inhibitors to 100 g of the crude ethyl-2-cyanoacrylate. The resulting mixture was distilled under a reduced pressure of 0.3 kPa so that 6.9 g of first fraction (7% low-boiling-point fraction) was distilled off. Then, 73.1 g of purified ethyl-2-cyanoacrylate (having a purity of 99%) was obtained as a main fraction of the distillation. Meanwhile, a high-boiling-point fraction (20% high-boiling-point fraction) including a later fraction and a still residue measured 20.3 g. Then, an adhesive composition was prepared by adding 0.0007 g of fluoroboric acid and 0.07 g of hydroquinone to 70 g of the purified ethyl-2-cyanoacrylate. A Hazen color number of the adhesive composition was measured to be 20. The adhesive composition was introduced in a polyethylene container and stored at a temperature of 70° C. for 1 week. Then, a Hazen color number of the adhesive composition was measured to be 50.

Example 10

To 100 g of the crude ethyl-2-cyanoacrylate obtained in Preparation Example 2, 3 g of pyrogallol was added and mixed, and then was left to stand still at a temperature of 20° C. for 2 days. Then, 0.5 g of hydroquinone and 0.1 g of phosphorus pentaoxide were added as polymerization inhibitors to 100 g of the crude ethyl-2-cyanoacrylate. A resultant mixture was distilled under a reduced pressure of 0.3 kPa so that 7.3 g of first fraction (7% low-boiling-point fraction) was distilled off. Then, 75.2 g of purified ethyl-2-cyanoacrylate (having a purity of 99%) was obtained as a main fraction of the distillation. Meanwhile, a high-boiling-point fraction (21% high-boiling-point fraction) including a later fraction and a still residue measured 20.9 g. Then, an adhesive composition was prepared by adding 0.0007 g of fluoroboric acid and 0.07 g of hydroquinone to 70 g of the purified ethyl-2-cyanoacrylate. A Hazen color number of the adhesive composition was measured to be 30. The adhesive composition was introduced in a polyethylene container and stored at a temperature of 70° C. for 1 week. Then, a Hazen color number of the adhesive composition was measured to be 60.

Example 11

To 100 g of the crude ethyl-2-cyanoacrylate obtained in Preparation Example 2, 2 g of pyrogallol was added and mixed, and then was left to stand still at a temperature of 30° C. for 5 days. Then, 0.5 g of hydroquinone and 0.1 g of phosphorus pentaoxide were added as polymerization inhibitors to 100 g of the crude ethyl-2-cyanoacrylate. The resulting mixture was distilled under a reduced pressure of 0.3 kPa so that 30.2 g of first fraction (30% low-boiling-point fraction) was distilled off. Then, 40.8 g of purified ethyl-2-cyanoacrylate (having a purity of 99%) was obtained as a main fraction of the distillation. Meanwhile, a high-boiling-point fraction (31% high-boiling-point fraction) including a later fraction and a still residue measured 31.3 g. Then, an adhesive composition was prepared by adding 0.0004 g of fluoroboric acid and 0.04 g of hydroquinone to 40 g of the purified ethyl-2-cyanoacrylate. A Hazen color number of the adhesive composition was measured to be 10. The adhesive composition was introduced in a polyethylene container and stored at a temperature of 70° C. for 1 week. Then, a Hazen color number of the adhesive composition was measured to be 40.

Example 12

To 100 g of the crude ethyl-2-cyanoacrylate obtained in Preparation Example 2, 1 g of resorcin was added and mixed, and then was left to stand still at a temperature of 30° C. for 2 days. Then, 0.5 g of hydroquinone and 0.1 g of phosphorus pentaoxide were added as polymerization inhibitors to 100 g of the crude ethyl-2-cyanoacrylate. The resulting mixture was distilled under a reduced pressure of 0.3 kPa so that 30.3 g of first fraction (30% low-boiling-point fraction) was distilled off. Then, 50.3 g of purified ethyl-2-cyanoacrylate (having a purity of 99%) was obtained as a main fraction of the distillation. Meanwhile, a high-boiling-point fraction (20% high-boiling-point fraction) including a later fraction and a still residue measured 20.4 g. Then, an adhesive composition was prepared by adding 0.0004 g of fluoroboric acid and 0.04 g of hydroquinone to 40 g of the purified ethyl-2-cyanoacrylate. A Hazen color number of the adhesive composition was measured to be 10. The adhesive composition was introduced in a polyethylene container and left to stand still at a temperature of 70° C. for 1 week. Then, a Hazen color number of the adhesive composition was measured to be 50.

Example 13

To 100 g of the crude ethyl-2-cyanoacrylate obtained in Preparation Example 3, 0.5 g of resorcin was added and mixed, and then was left to stand still at a temperature of 20° C. for 1 day. Then, 0.5 g of hydroquinone and 0.1 g of phosphorus pentaoxide were added as polymerization inhibitors to 100 g of the crude ethyl-2-cyanoacrylate. The resulting mixture was distilled under a reduced pressure of 0.3 kPa so that 20.2 g of first fraction (20% low-boiling-point fraction) was distilled off. Then, 60.5 g of purified ethyl-2-cyanoacrylate (having a purity of 99%) was obtained as a main fraction of the distillation. Meanwhile, a high-boiling-point fraction (20% high-boiling-point fraction) including a later fraction and a still residue measured 19.9 g. Then, an adhesive composition was prepared by adding 0.0005 g of fluoroboric acid and 0.05 g of hydroquinone to 50 g of the purified ethyl-2-cyanoacrylate. A Hazen color number of the adhesive composition was measured to be 10. The adhesive composition was introduced in a polyethylene container and stored at a temperature of 70° C. for 1 week. Then, a Hazen color number of the adhesive composition was measured to be 50.

Example 14

To 100 g of the crude ethyl-2-cyanoacrylate obtained in Preparation Example 4, 1 g of gallic acid was added and mixed, and then was left to stand still at a temperature of 30° C. for 5 days. Then, 0.5 g of hydroquinone and 0.1 g of phosphorus pentaoxide were added as polymerization inhibitors to 100 g of the crude ethyl-2-cyanoacrylate. The resulting mixture was distilled under a reduced pressure of 0.3 kPa so that 10.2 g of first fraction (10% low-boiling-point fraction) was distilled off. Then, 60.5 g of purified ethyl-2-cyanoacrylate (having a purity of 99%) was obtained as a main fraction of the distillation. Meanwhile, a high-boiling-point fraction (30% high-boiling-point fraction) including a later fraction and a still residue measured 30.3 g. Then, an adhesive composition was prepared by adding 0.0005 g of fluoroboric acid and 0.05 g of hydroquinone to 50 g of the purified ethyl-2-cyanoacrylate. A Hazen color number of the adhesive composition was measured to be 30. The adhesive composition was introduced in a polyethylene container and stored at a temperature of 70° C. for 1 week. Then, a Hazen color number of the adhesive composition was measured to be 60.

Example 15

To 100 g of the crude ethyl-2-cyanoacrylate obtained in Preparation Example 4, 3 g of pyrogallol was added and mixed, and then was left to stand still at a temperature of 30° C. for 5 days. Then, 0.5 g of hydroquinone and 0.1 g of phosphorus pentaoxide were added as polymerization inhibitors to 100 g of the crude ethyl-2-cyanoacrylate. The resulting mixture was distilled under a reduced pressure of 0.3 kPa so that 30.3 g of first fraction (30% low-boiling-point fraction) was distilled off. Then, 51.6 g of purified ethyl-2-cyanoacrylate (having a purity of 99%) was obtained as a main fraction of the distillation. Meanwhile, a high-boiling-point fraction (21% high-boiling-point fraction) including a later fraction and a still residue measured 21.0 g. Then, an adhesive composition was prepared by adding 0.0005 g of fluoroboric acid and 0.05 g of hydroquinone to 50 g of the purified ethyl-2-cyanoacrylate. A Hazen color number of the adhesive composition was measured to be 10. The adhesive composition was introduced in a polyethylene container and stored at a temperature of 70° C. for 1 week. Then, a Hazen color number of the adhesive composition was measured to be 50.

TABLE 1

| | Preparation Ex. No. | Hazen Color Number | Polyhydric Aromatic Compound | Additive Amount (wt %) | Storage Temperature (° C.) | Storage Period (Day) |
|---|---|---|---|---|---|---|
| Comp. Ex. 1 | 1 | 150 | — | — | — | — |
| Comp. Ex. 2 | 1 | 150 | — | — | — | — |
| Comp. Ex. 3 | 2 | 150 | Resorcin | 0.1 | 40 | 2 |
| Comp. Ex. 4 | 2 | 150 | 2,6-di-tert-butylphenol | 0.1 | 40 | 2 |
| Comp. Ex. 5 | 2 | 150 | Resorcin | 1 | 20 | 5 |
| Comp. Ex. 6 | 2 | 150 | Pyrogallol | 1 | 40 | 5 |
| Comp. Ex. 7 | 2 | 150 | Gallic Acid Methoxyethyl Ester | 0.5 | 40 | 1 |
| Comp. Ex. 8 | 3 | 80 | — | — | — | — |
| Comp. Ex. 9 | 3 | 80 | Gallic Acid | 1 | 20 | 5 |
| Comp. Ex. 10 | 3 | 80 | Catechol | 1 | 30 | 5 |

TABLE 2

| | Low-boiling-point Fraction Removal Ratio | High-boiling-point Fraction Removal Ratio | Initial Hazen Color Number | Hazen Color Number After 1 Week of Storage at Temperature of 70° C. |
|---|---|---|---|---|
| Comp. Ex. 1 | 3% | 15% | 60 | 120 |
| Comp. Ex. 2 | 30% | 30% | 60 | 100 |
| Comp. Ex. 3 | — | — | 70 | 120 |
| Comp. Ex. 4 | 3% | 15% | 80 | 120 |
| Comp. Ex. 5 | 3% | 15% | 70 | 110 |
| Comp. Ex. 6 | 3% | 15% | 60 | 110 |
| Comp. Ex. 7 | 4% | 20% | 60 | 90 |
| Comp. Ex. 8 | 30% | 30% | 60 | 100 |
| Comp. Ex. 9 | 3% | 21% | 60 | 90 |
| Comp. Ex. 10 | 30% | 21% | 60 | 100 |

TABLE 3

| | Preparation Ex. No | Hazen Color Number | Polyhydric Aromatic Compound | Additive Amount (wt %) | Storage Temperature (° C.) | Storage Period (Day) |
|---|---|---|---|---|---|---|
| Ex. 1 | 1 | 150 | Gallic Acid Methoxyethyl Ester | 0.1 | 40 | 2 |
| Ex. 2 | 1 | 150 | Gallic Acid Methoxyethyl Ester | 2 | 40 | 1 |
| Ex. 3 | 1 | 150 | Gallic Acid Methoxyethyl Ester | 0.5 | 20 | 10 |
| Ex. 4 | 1 | 150 | Gallic Acid | 0.1 | 20 | 10 |
| Ex. 5 | 1 | 150 | Gallic Acid | 0.1 | 20 | 10 |
| Ex. 6 | 2 | 150 | Pyrogallol | 1 | 10 | 15 |
| Ex. 7 | 2 | 150 | Pyrogallol | 1 | 30 | 15 |
| Ex. 8 | 2 | 150 | Resorcin | 5 | 20 | 30 |
| Ex. 9 | 1 | 150 | Gallic Acid | 1 | 20 | 1 |
| Ex. 10 | 2 | 150 | Pyrogallol | 3 | 20 | 2 |
| Ex. 11 | 2 | 150 | Pyrogallol | 2 | 30 | 5 |
| Ex. 12 | 2 | 150 | Resorcin | 1 | 30 | 2 |
| Ex. 13 | 3 | 80 | Resorcin | 0.5 | 20 | 1 |
| Ex. 14 | 4 | 250 | Gallic Acid | 1 | 30 | 5 |
| Ex. 15 | 4 | 250 | Pyrogallol | 3 | 30 | 5 |

TABLE 4

| | Low-boiling-point Fraction Removal Ratio | High-boiling-point Fraction Removal Ratio | Initial Hazen Color Number | Hazen Color Number After 1 Week of Storage at Temperature of 70° C. |
|---|---|---|---|---|
| Ex. 1 | 10% | 20% | 30 | 50 |
| Ex. 2 | 10% | 20% | 30 | 50 |
| Ex. 3 | 10% | 20% | 20 | 40 |
| Ex. 4 | 5% | 10% | 30 | 50 |
| Ex. 5 | 40% | 30% | 10 | 30 |
| Ex. 6 | 20% | 20% | 30 | 40 |
| Ex. 7 | 20% | 15% | 30 | 50 |
| Ex. 8 | 15% | 20% | 30 | 80 |
| Ex. 9 | 7% | 20% | 20 | 50 |
| Ex. 10 | 7% | 21% | 30 | 60 |
| Ex. 11 | 30% | 31% | 10 | 40 |
| Ex. 12 | 30% | 20% | 10 | 50 |
| Ex. 13 | 20% | 20% | 10 | 50 |
| Ex. 14 | 10% | 30% | 30 | 60 |
| Ex. 15 | 30% | 21% | 10 | 50 |

INDUSTRIAL APPLICABILITY

As described above, according to a 2-cyanoacrylate-purifying method of the present invention, a 2-cyanoacrylate which has been colored is decolored and the 2-cyanoacrylate thus decolored is prevented from being further colored (is improved in hue stability). Therefore, the 2-cyanoacrylate-purifying method of the present invention is suitably applicable and very useful in a field where an adhesive composition is required to be transparent.

The invention claimed is:

1. A 2-cyanoacrylate-purifying method for purifying a crude 2-cyanoacrylate having a Hazen color number of 50 or more, the 2-cyanoacrylate being represented by formula (2):

(2)

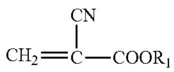

wherein $R_1$ represents an aliphatic hydrocarbon group, an alicyclic hydrocarbon group or an aromatic hydrocarbon group which is saturated or unsaturated and may be substituted with a C1 to C16 substituent, said 2-cyanoacrylate-purifying method comprising the steps of:

(a) adding to, the crude 2-cyanoacrylate, at least one kind of a polyhydric aromatic compound selected from the group consisting of resorcin and a compound represented by formula (1):

(1)

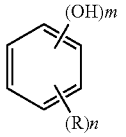

wherein R independently represents a hydrogen atom, a carboxy group, an alkoxycarbonyl group, or an alkoxyalkyloxycarbonyl group; and m is an integer of 3 to 5, n is an integer of 1 to 3, and m +n =6;

(b) storing, at a temperature in a range of 0 ° C. to 40 ° C. for 0.5 day or more, the resulting mixture obtained in the step (a); and (c) subjecting the mixture to reduced pressure distillation so as to remove (i) a low-boiling-point fraction by 5 wt % to 40 wt % with respect to the crude 2-cyanoacrylate, and (ii) a high-boiling-point fraction by 10 wt % to 30 wt % with respect to the crude 2-cyanoacrylate, so as to obtain a purified 2-cyanoacrylate having a Hazen color number of 40 or less.

2. The 2-cyanoacrylate-purifying method as set forth in claim 1, wherein the polyhydric aromatic compound is at least one kind selected from the group consisting of gallic acid, gallic acid alkyl esters containing a C1 to C4 alkyl group, gallic acid alkoxyalkyl esters containing a C1 to C4 alkoxyalkyl group, pyrogallol, 1,2,4-trihydroxybenzene, phloroglucinol, and resorcin.

3. The 2-cyanoacrylate-purifying method as set forth in claim 1, wherein the low-boiling-point fraction is removed by 10 wt % to 30 wt % with respect to the crude 2-cyanoacrylate during the reduced pressure distillation.

4. The 2-cyanoacrylate-purifying method as set forth in claim 2, wherein the low-boiling-point fraction is removed by 10 wt % to 30 wt % with respect to the crude 2-cyanoacrylate during the reduced pressure distillation.

* * * * *